United States Patent [19]

Fujisawa et al.

[11] 4,219,659

[45] Aug. 26, 1980

[54] PROCESS FOR THE PREPARATION OF THIOPHENE DERIVATIVES AND THIOPHENE DERIVATIVES OBTAINED THERETHROUGH

[75] Inventors: Tamotsu Fujisawa; Kunikazu Sakai, both of Yamato; Akira Kurebayashi, Tokyo, all of Japan

[73] Assignee: Sagami Chemical Research Center, Tokyo, Japan

[21] Appl. No.: 910,290

[22] Filed: May 30, 1978

[30] Foreign Application Priority Data

Jul. 21, 1977 [JP] Japan .................................. 52/86606
Jul. 21, 1977 [JP] Japan .................................. 52/86607

[51] Int. Cl.$^2$ .................... C07D 333/24; C07D 333/28
[52] U.S. Cl. ........................................ 549/79; 549/78
[58] Field of Search ................ 260/332.2 A, 332.2 C, 260/332.3; 549/78, 79

[56] References Cited

U.S. PATENT DOCUMENTS

| | | | |
|---|---|---|---|
| 2,226,645 | 12/1940 | Thomas et al. .................... | 560/212 |
| 2,921,940 | 1/1960 | Ransden ........................ | 260/332.2 R |
| 3,097,206 | 4/1963 | Zirkle ............................ | 260/332.2 R |

OTHER PUBLICATIONS

Blumbergs, P. et al., *J. Org. Chem.*, vol. 37 (1972), pp. 1248–1251.
Hartough, Howard D., "Thiophenye and Its Derivatives." Interscience Publ. (1952), pp. 344–349 at p. 349.
Roberts, John D. et al., "Basic Principles of Organic Chemistry." W. A. Benjamin, Publ. (1973), pp. 492–493.

*Primary Examiner*—Natalie Trousof
*Assistant Examiner*—L. Hendriksen
*Attorney, Agent, or Firm*—Frishauf, Holtz, Goodman & Woodward

[57] ABSTRACT

An α-(2-thienyl)propionic acid can easily be prepared in a high yield and high selectivity by reacting a 2-(dihaloacetyl)thiophene which is easily obtainable by acetylation and halogenation of a substituted or unsubstitued thiophene, with a methylmetal compound and then reacting an alkali metal hydroxide with the reaction product. α-(2-Thienyl)propionic acids are useful compounds from which, for example, thioprofenic acid can easily be prepared. Thioprofenic acid is known as an anti-inflammatory agent. As reaction intermediates, 1-(2-thienyl)-1-dihalomethylethanols can be obtained. Which are novel and useful compounds.

6 Claims, No Drawings

PROCESS FOR THE PREPARATION OF THIOPHENE DERIVATIVES AND THIOPHENE DERIVATIVES OBTAINED THERETHROUGH

BACKGROUND OF THE INVENTION

1. Field of the Invention

The present invention relates to a process for the preparation of thiophene derivatives and novel thiophene derivatives, and in more detail, this invention relates to a process for preparing α-(2-thienyl)propionic acids which are useful as, for example, starting raw materials for the production of thioprofenic acid which is known as an anti-inflammatory agent, from 2-(dihaloacetyl)thiophenes which are easily obtainable by acetylation and halogenation of substituted or unsubstituted thiophenes. This invention also relates to novel compounds, i.e. 1-(2-thienyl)-1-dihalomethylethanols which are obtainable during the course of the preparation of α-(2-thienyl)propionic acids.

2. Description of the Prior Art

The processes for the preparation of α-(2-thienyl)propionic acids hitherto known in the art are (1) a process which comprises chloromethylation of thiophene by treating with aqueous formaldehyde in concentrated hydrochloric acid to obtain 2-thienylmethyl chloride, and introduction of cyano group treating with sodium cyanide to transfer into 2-thienylacetonitrile, then converting it to ethyl thienylcyanoacetate by ethoxycarbonation with diethyl carbonate in the presence of sodium metal, and then reacting the ester with methyl iodide in the presence of a base to prepare ethyl α-thienyl-α-cyanopropionate, then converting it to α-thienylpropionitrile by conducting hydrolysis and decarboxylation and then, further conducting hydrolysis of nitrile group to convert it to carboxyl group (M. Bercot-Vatteroni et al., Bull. Soc. Chim., France, 1820 (1961)) and (2) a process which comprises condensating ethyl chloroglyoxalate with thiophene by the liberation of hydrogen chloride, then conducting hydrolysis of the ester and reacting the product with a Grignard reagent thereby converting the carbonyl group to a methyl carbinol group and finally reducing the hydroxyl group to a hydrogen atom (F. Clemence et al., Eur. J. Med. Chem., (1974-9), 390). However, these processes are difficult to adopt as industrial processes for the production of α-(2-thienyl)propionic acids, since these processes need many reaction stages and are complicated and in process (1), obtainment of a starting material, i.e. thienylcyanoacetate is difficult.

SUMMARY OF THE INVENTION

We have found that 1-(2-thienyl)-1-dihalomethyl ethanols, which are novel compounds, can be prepared in high yields by reacting 2-(dihaloacetyl)thiophenes which are easily prepared industrially by a process developed recently by us, with a methylmetal compound and have also found that said dihalomethylethanols can easily be converted in high yields to α-(2-thienyl)propionic acids by treating them with an alkali metal hydroxide and thus, completed the present invention.

To assist the understanding of the present invention, the process and the products of the invention are given in a chemical scheme:

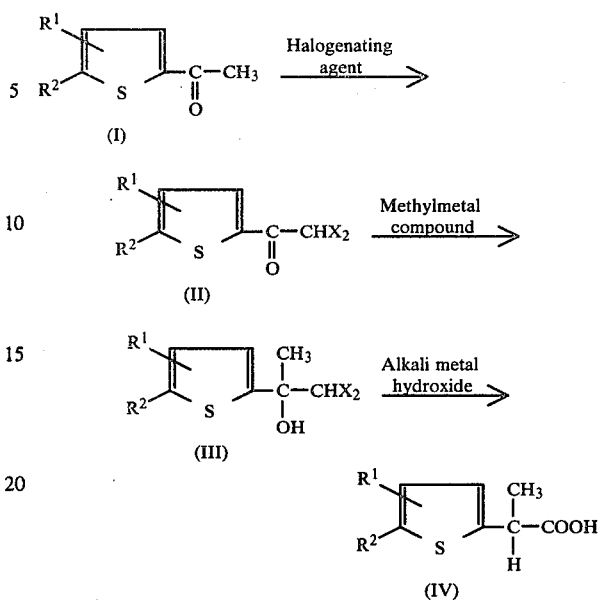

In the scheme shown above, $R^1$ is selected from the group consisting of hydrogen atom and lower alkyl groups, $R^2$ is selected from the group consisting of hydrogen atom, substituted or unsubstituted hydrocarbon radicals and halogen atom, and X is a halogen atom.

Accordingly, the object of this invention is to give a process for preparing 1-(2-thienyl)-1-dihalomethylethanols from 2-(dihaloacetyl)thiophenes. Another object of this invention is to provide a process for preparing α-(2-thienyl)propionic acids from 2-(dihaloacetyl)thiophenes. Further objects of this invention are to provide a process for preparing 1-(2-thienyl)-1-dihalomethylethanols from 2-acetylthiophenes and also to provide a process for preparing α-(2-thienyl)propionic acids from 2-acetylthiophenes. Still further object of this invention is to provide novel compounds, namely 1-(2-thienyl)-1-dihalomethylethanols. Other objects of this invention will become apparent during the following detailed descriptions of the invention.

DETAILED DESCRIPTION OF THE INVENTION

In the process for preparing 1-(2-thienyl)-1-dihalomethylethanols of this invention, it is an indispensable requirement to react a 2-(dihaloacetyl)thiophene with a methylmetal compound.

However, 2-(dihaloacetyl)thiophenes per se are almost not known by the persons skilled in the art and therefore, a process for the production of 2-(dihaloacetyl)thiophenes will be explained at first.

2-(Dihaloacetyl)thiophenes can be prepared by reacting a 2-acetylthiophenes with a halogenating agent. As examples of the 2-acetylthiophenes, 2-acetylthiophene, 2-acetylthiophenes having a lower alkyl group such as methyl, ethyl, propyl, butyl group, etc. at 3- or 4-position of the thiophene ring, 4-methyl-5-substituted benzyl-2-acetylthiophene, 4-ethyl-5-chloro-2-acetylthiophene, 4-methyl-5-(p-chloro-α-substituted benzyl)-2-acetylthiophene, etc. can be shown. Also, as examples of the halogenating agent which is the other starting material of the process for the production of 2-(dihaloacetyl)thiophenes, chlorine, bromine, sulfuryl chloride, sulfuryl bromide, t-butyl hypochlorite, selenium oxychloride, N-chlorosuccinimide, etc. can be shown. The use of chlorine or bromine is preferred in an industrial and commercial production. The reaction is, preferably, conducted in the presence of a solvent such as a halogenated hydrocarbon, e.g. carbon tetrachloride, methylene chloride, chloroform, etc. or a polar solvent, e.g. an aliphatic carboxylic acid including acetic acid, propionic acid, butyric acid, etc. The use of an aliphatic carboxylic acid is preferred in order to minimize the formation of by-products. The reaction can be carried out within a temperature range of from 0° C. to the boiling point of the solvent used, but the use of a temperature of from 0° C. to 50° C. is usually sufficient and preferred to avoid the formation of by-products.

2-(Dihaloacetyl)thiophenes thus prepared can be used not only as a starting material for the preparation of α-(2-thienyl)propionic acids of the present invention but also as a starting material for the preparation of 2-thiopheneacetic acids which are useful and have wide demands as chemical modifiers of penicillin and cephalosporin, for example.

As aforementioned, in the process for preparing 1-(2-thienyl)-1-dihalomethylethanols of this invention, it is necessary, as the indispensable reaction, to react a 2-(dihaloacetyl)thiophene with a methylmetal compound. Relative to the 2-(dihaloacetyl)thiophenes, as the persons skilled in the art can easily understand from the explanation given above, 2-(dichloroacetyl)thiophene, 2-(dibromoacetyl)thiophene, 4-methyl-2-(dichloroacetyl)thiophene, 3-methyl-2-(dichloroacetyl)thiophene, 4-ethyl-2-(dibromoacetyl)thiophene, 5-chloro-2-(dichloroacetyl)thiophene, 5-(α-substituted benzyl)-2-(dichloroacetyl)thiophene, 4-methyl-5-(p-chloro-α-substituted benzyl)-2-(dichloroacetyl)thiophene, etc. can be shown.

Also, as the other starting material, i.e. a methylmetal compound, such as methylmagnesium iodide, methyl-magnesium bromide, methylmagnesium chloride, methyllithium, dimethylzinc, methylzinc chloride, etc. can be shown.

In the practice of this step of the process of the present invention, the use of a solvent is preferred and a wide variety of solvents, for example, linear and cyclic ethers such as diethylether, dimethoxyethane, tetrahydrofuran, dioxane, etc. and hydrocarbon solvents such as benzene, hexane, etc. can be employed. In the practice of the methylation reaction of this invention, the use of an equimolar amount of or a small excess amount of a methylmetal compound per one mole of 2-(dihaloacetyl)thiophene is preferred and the reaction can be conducted within a temperature range of from −100+ C. to +50° C. The use of a temperature between −78° C. to room temperature is preferred in the view point of reaction velocity and to avoid the formation of by-products. The reaction is carried out in an essentially anhydrous condition. Under the conditions as stated above, the reaction may, usually, be completed within a range of 5–24 hours. Then, the reaction product is treated with water.

The 1-(2-thienyl)-1-dihalomethylethanols thus prepared are novel compounds from which useful compounds, α-(2-thienyl)propionic acids can easily be prepared. In the dihalomethylethanols, 1-(2-thienyl)-1-dichloromethylethanol, for example, has following physical properties:
Boiling point: 78°–84° C./0.05 mmHg.
NMR (CDCl$_3$)δ: 1.84 (3H, s), 2.70 (1H, broad s), 5.85 (1H, s), 7.20 (3H).

IR (liquid film): 3450, 3100, 2980, 1380, 1100, 792, 705 cm$^{-1}$.
MS (70 eV) m/e: 194 (2.0%), 192 (2.6%) (M$^+$−H$_2$O), 163 (2.3%), 161 (6.5%), 127 (61.3%) (M$^+$−CHCl$_2$).

In the process for preparing α-(2-thienyl)propionic acids from 1-(2-thienyl)-1-dihalomethylethanols, it is an indispensable requirement to treat a 1-(2-thienyl)-1-dihalomethylethanol with an alkali metal hydroxide.

As the alkali metal hydroxide, sodium hydroxide, potassium hydroxide, etc. can be shown and anyone of them can be used, but the use of sodium hydroxide or potassium hydroxide is preferred. In the practice of this step of the present invention, it is preferred to use a non-polar solvent. As the non-polar solvent, n-hexane, benzene, etc. can be shown. The reaction can be carried out in a temperature range of 0° C.–50° C., but is preferably conducted at room temperature from the view point of easy operation. In this case, one of the starting materials, i.e. a 1-(2-thienyl)-1-dihalomethylethanol is in liquid phase whereas the other raw material, i.e. an alkali metal hydroxide is in solid state and therefore, the reaction proceeds in a form of, so called as liquid-solid contact reaction, that is a heterogenious reaction system, and accordingly, it is necessary to use an excess amount of an alkali metal hydroxide. It is preferable to use an alkali metal hydroxide in an amount of more than 3 moles per one mole of a 1-(2-thienyl)-1-dihalomethylethanol and more preferably 5–10 moles of an alkali metal hydroxide is used per one mole of said dihalomethylethanol.

DESCRIPTION OF THE PREFERRED EMBODIMENTS

In the following, the invention will be explained in more detailed and material fashion by illustration of Examples, however, it is to be noted that these Examples are given only for the purpose of illustration and are not to be considered as limiting the present invention thereto.

EXAMPLE 1

2-Acetylthiophene (6.31 g, 50.0 mmol) was dissolved in glacial acetic acid (25 ml) and chlorine gas was bubbled into the solution under water cooling. The supply of cooling water was so adjusted that the temperature of the reaction system was kept below 28° C. After passing chlorine gas for about 2 hours, the reaction was completed and the reaction solution showed a slight yellow color. At this point, the introduction of chlorine gas was stopped and the reaction solution was poured onto 150 ml of crushed ice and was extracted with diethylether. The ether layer was washed with cold water and then dried with anhydrous sodium sulfate. After removal of the ether under a reduced pressure, 9.8 g of 2-(dichloroacetyl)thiophene was obtained as an oily substance. The value of 9.8 g is the quantitative yield.

EXAMPLE 2

Under an argon atmosphere, 0.54 g of magnesium turnings (22 mg atom) was mixed with dry diethylether (15 ml), and 3.72 g of methyl iodide (93% purity, 24 mmol) solution in dry diethylether (15 ml) was dropped gradually thereto to prepare Grignard reagent of methylmagnesium iodide. The Grignard reagent was gradually added in drop-wise into 3.60 g of 2-(dichloroacetyl)thiophene (18.5 mmol) solution in dry diethylether (15 ml) with cooling in an ice-water bath so as to maintain a temperature below 10° C. After the dropwise addition was completed, the reaction mixture was agitated over a night at room temperature, and then, 20 ml of a saturated aqueous solution of ammonium chloride was added thereto and extracted with ether. The ether layer was washed with a saturated aqueous solution of sodium chloride and dried over anhydrous sodium sulfate and the ether was distilled off. Thus, 1-(2-thienyl)-1-dichloromethylethanol was obtained in an amount of 3.22 g (yield 83%).
Boiling point: 78°–84° C./0.05 mmHg.
NMR (CDCl$_3$)δ: 1.84 (3H, s), 2.70 (1H, broad s), 5.85 (1H, s), 7.20 (3H).
IR (liquid film): 3450, 3100, 2980, 1380, 1100, 792, 705 cm$^{-1}$.
MS (70 eV) m/e: 194 (2.0%), 192 (2.6%) (M$^+$ −H$_2$O), 163 (2.3%), 161 (6.5%), 127 (61.3%) (M$^+$ −CHCl$_2$).

EXAMPLE 3

In 40 ml of benzene, 3.93 g of sodium hydroxide (98 mmol) was crushed finely. Under vigorous agitation, 2.09 g of 1-(2-thienyl)-1-dichloromethylethanol (9.9 mmol) was added thereto and agitated for 24 hours at room temperature and then 20 ml of water was added thereto under ice cooling. After washing the diethylether, the aqueous alkaline solution was neutralized (about pH 2) with 6 N hydrochloric acid and extracted with diethylether. The ether layer was washed with a saturated aqueous solution of sodium chloride and dried over anhydrous sodium sulfate and then the ether was distilled off. Thus, 1.22 g of α-(2-thienyl)propionic acid was obtained (yield 79%).
NMR (CDCl$_3$)δ: 1.57 (3H, d, J=7.0 Hz), 4.01 (1H, q, J=7.0 Hz), 7.0 (3H), 9.5 (1H, broad s).
IR (liquid film): 3400-2500 (broad), 1710, 700 cm$^{-1}$.

We claim:

1. A process for preparing an α-(2-thienyl)-propionic acid comprising reacting a 2-(dihaloacetyl)-thiophene of the formula

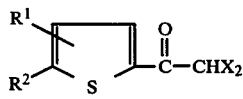

wherein R$^1$ is selected from the group consisting of hydrogen atom and lower alkyl radicals, R$^2$ is selected from the group consisting of a hydrogen atom, hydrocarbon radicals and halogen atom, and X is a halogen atom, with a methylmetal compound selected from the group consisting of methylmagnesium halide, methyllithium, dimethylzinc and methylzinc halide under essentially anhydrous conditions in the presence of a solvent and then treating the reaction product with water, thereby forming a 1-(2-thienyl)-1-dihalomethylethanol of the formula

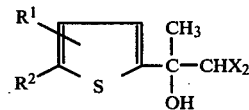

and reacting said 1-(2-thienyl)-1-dihalomethylethanol with an alkali metal hydroxide to form an α-(2-thienyl)-propionic acid of the formula

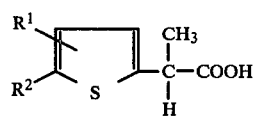

2. A process of claim 1, wherein R$^1$ is a hydrogen atom or a methyl radical, R$^2$ is a hydrogen atom, and X is a chlorine or bromine atom, and the methylmetal compound is a methylmagnesium halide.

3. A process of claim 1, wherein the methylation is carried out in the presence of a solvent selected from the group consisting of ethers and hydrocarbons at a temperature of from −78° C. to room temperature, and the reaction with an alkali metal hydroxide is carried out in the presence of a non-polar solvent at a temperature of 0°–50° C.

4. A process of claim 2, wherein 2-(dichloroacetyl)-thiophene prepared by a reaction of a 2-acetylthiophene represented by the general formula:

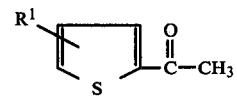

with chlorine in the presence of an aliphatic carboxylic acid solvent at a temperature of 0°–50° C. is used as a starting material (in the formula, R$^1$ represents a hydrogen atom or a methyl radical).

5. A 1-(2-thienyl)-1-dihalomethylethanol represented by the general formula:

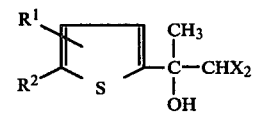

wherein R$^1$ is selected from the group consisting of hydrogen atom and lower alkyl radicals, R$^2$ is selected from the group consisting of hydrogen atom, substituted or unsubstituted hydrocarbon radicals and halogen atom and X represents a halogen atom.

6. A product of claim 5, wherein R$^1$ is a hydrogen atom or a methyl radical, R$^2$ is a hydrogen atom, and X is a chlorine or bromine atom.

* * * * *